United States Patent [19]
Minshull et al.

[11] Patent Number: 5,823,222
[45] Date of Patent: Oct. 20, 1998

[54] SANITARY SAMPLING DEVICE AND METHOD FOR USING SAME

[75] Inventors: James Edward Minshull, Coquitlam; Robert G. Lawrence, Delta, both of Canada

[73] Assignee: Labatt Brewing Company Limited, London, Canada

[21] Appl. No.: 758,563

[22] Filed: Nov. 29, 1996

Related U.S. Application Data

[60] Provisional application No. 60/029,210, Oct. 31, 1996.

[51] Int. Cl.$^6$ .............................. G01N 1/10; B08B 3/04; F16L 37/32; F16K 43/00
[52] U.S. Cl. ................... 137/15; 73/863.86; 134/166 C; 137/240; 137/322; 137/614.04; 141/1; 141/83; 141/89; 222/148; 422/103
[58] Field of Search ............... 137/322, 614.02, 137/15, 240, 614.03, 614.04, 614.05; 141/2, 10, 83, 85, 89, 1; 73/863.81, 863.85, 863.86; 251/149.6; 422/68.1, 81, 103; 134/166 R, 166 C; 222/148

[56] References Cited

U.S. PATENT DOCUMENTS

| Re. 32,695 | 6/1988 | Nahra et al. ........................ 261/118 |
| 2,610,123 | 9/1952 | Bruyere et al. ....................... 426/15 |
| 2,948,661 | 8/1960 | O'Neill, Jr. ......................... 435/286.5 |
| 3,176,717 | 4/1965 | Ogne ................................. 137/614.02 |
| 3,392,034 | 7/1968 | Barnes ................................... 426/397 |
| 3,589,270 | 6/1971 | Schlimme et al. ................... 99/277.2 |
| 3,616,261 | 10/1971 | Leue et al. ............................ 99/278 |
| 3,627,544 | 12/1971 | Bosewitz et al. ..................... 99/276 |
| 3,674,051 | 7/1972 | Stratman ........................... 137/614.02 |
| 3,913,608 | 10/1975 | Johnston ............................... 137/322 |
| 3,962,478 | 6/1976 | Hohlbein et al. ..................... 99/278 |
| 4,002,186 | 1/1977 | Fink et al. ......................... 137/614.03 |
| 4,035,893 | 7/1977 | Zurit et al. ........................... 137/322 |
| 4,159,102 | 6/1979 | Fallon et al. ......................... 137/322 |
| 4,233,407 | 11/1980 | Seebeck et al. ....................... 99/276 |
| 4,268,479 | 5/1981 | Webster ................................ 422/103 |
| 4,329,433 | 5/1982 | Seebeck et al. ....................... 99/276 |
| 4,343,231 | 8/1982 | Devreux ............................. 99/277.2 |
| 4,350,503 | 9/1982 | Skoli et al. ........................ 99/277.2 |
| 4,363,336 | 12/1982 | Cerrato ................................. 137/212 |
| 4,394,874 | 7/1983 | Walter ............................. 137/614.02 |
| 4,406,301 | 9/1983 | Cerrato ................................. 137/212 |
| 4,408,631 | 10/1983 | Uhlig et al. ........................... 137/380 |
| 4,510,969 | 4/1985 | Rodth ................................... 137/322 |
| 4,736,926 | 4/1988 | Fallon et al. ......................... 137/322 |
| 4,890,642 | 1/1990 | Smazik et al. ..................... 137/614.03 |
| 4,949,745 | 8/1990 | McKeon ................................. 137/15 |
| 4,989,630 | 2/1991 | Yonezawa ............................. 137/240 |
| 5,088,519 | 2/1992 | Giroux et al. ....................... 137/240 |
| 5,127,276 | 7/1992 | Prentiss ............................. 73/863.86 |
| 5,144,979 | 9/1992 | Shobuzako et al. ............... 137/614.02 |
| 5,146,792 | 9/1992 | Iff ..................................... 73/863.86 |
| 5,235,901 | 8/1993 | MacLennan et al. .................... 99/276 |
| 5,296,197 | 3/1994 | Newberg et al. ..................... 137/240 |
| 5,311,899 | 5/1994 | Isayama et al. ...................... 137/240 |
| 5,348,192 | 9/1994 | Sardynski et al. ................... 137/240 |
| 5,365,830 | 11/1994 | MacLennan et al. .................... 99/276 |
| 5,479,955 | 1/1996 | Roodvoets et al. ..................... 137/15 |

Primary Examiner—George L. Walton
Attorney, Agent, or Firm—Cammarata & Grandinetti

[57] ABSTRACT

A sanitary coupling device and a method for its use are described. The sanitary coupling device taps a vessel, such as a brewery tank, without exposing the fluid to the atmosphere. The device can include a coupler that prevents the collected fluid from exposure to the atmosphere. The method for tapping a vessel can include engaging a nipple with a coupler. Then, collecting a sample and disengaging the coupler from the nipple is performed. The invention is desirable for a brewery tank sampling with a clean-in-place connection system.

3 Claims, 5 Drawing Sheets

SANITARY SAMPLING DEVICE AND METHOD FOR USING SAME

The applicants claim the benefits of U.S. Provisional application Ser. No. 60/029,210 filed on Oct. 31, 1996, now abandoned.

BACKGROUND OF THE INVENTION

1. Field of the Invention

This invention relates to a sanitary sampling device and a method for using a sanitary sampling device. Specifically, this invention relates to self-sealing nozzles that permit sampling from vats or tanks and methods of the using such nozzles.

2. Description of the Background Art

Numerous industries use large vats or tanks for preparing, treating, or holding liquid substances. Many liquid substances must be routinely sampled while in these vats or tanks. The samples of the liquid substances permit analysis to occur during processing. The analysis of the samples can be for biological components, chemical reactants, and/or immediate compounds occurring in the liquid substances during processing. Examples of such liquid substances include liquids from the food industry such as dairy and cheese liquids, cider and soft liquids, and malt beverage and wine liquids. Liquids from other industries such as the pharmaceutical industry also require periodic testing.

Vats or tanks are traditionally fitted with faucets or spigots. These fittings are coupled to the vat or tank by threads or welding. The liquid from the vat or tank flows into the fitting. The flow of the liquid through the fitting is prevented by a stop valve located in the fitting. The stop valve is attached to a handle or means for operating the stop valve. The handle, when turned, opens the stop valve and permits the liquid to flow through an orifice in the stop valve and into a nozzle of the fitting. The sample of the liquid can be obtained by holding another vessel under the nozzle and collecting the effluent of the liquid until the stop valve is closed.

Closing the stop valve terminates the flow of liquid from the vat or tank. However, residual liquid remains in the nozzle unless the nozzle is cleaned. When the residual liquid is aqueous, the liquid can foster the growth of microorganisms such as bacteria. Bacteriological growth is especially prevalent when the liquid contains nutrients such as sugars and starches. Nutrients are particularly prevalent in liquids that are processed by the brewing industry.

Liquids processed by the brewing industry include mash, wort, and green beer. These liquids contain sugars, starches, and other nutrients. These liquids can be contaminated during processing by bacteria or other undesirable microorganisms. Consequently, frequent testing of these liquids is performed during the processing of the liquid. A significant financial benefit is realized by early detection of microbial contamination.

Early detection of microbial contamination permits a brewer to terminate the processing of a contaminated "batch" or vat of wort, green beer, or malt beverage. Brewing processes require significant holding times for the various processing steps. Reducing the time a tank or other equipment contains contaminated material improves the efficiency of the brewing process. However, the discarding of a batch of material that is inaccurately identified as contaminated is also a significant expense to a brewer.

Test samples from brewing vats or tanks are often contaminated during the process of acquiring the sample. If precautions are not exercised to prevent exposure of the sample to the environment, the sample, during its collection, can acquire microbes that are not present in the vat or tank. The fittings mounted on vats and tanks provide a constant source for such contamination.

Fittings, such as a faucet or a spigot, have a channel or a spout that extends from a stop valve to the terminus or exit of the faucet or spigot. When the stop valve of a faucet or spigot is closed, the liquid drains from the stop valve through the channel or port and past the exit of the faucet or spigot. However, a portion of the liquid adheres to the wall of the channel or port.

The liquid, that remains in the channel, is exposed to the atmosphere and fosters the growth of microbes from the atmosphere. The microbes grown in the channel are flushed from the channel when the next sample is taken from the vat or tank. In this manner, the test of the subsequent sample indicates the presence of contaminants. However, the contaminants are not present in liquid in the vat or tank.

U.S. Pat. No. 4,268,479 to Webster discloses a fluid analyzer. The fluid analyzer is portable and engages a discharge port of a zwickel fitting or similar device. The zwickel fitting can be mounted on a vat or brewery vessel. A tip of the fluid analyzer inserts into the discharge port and downstream from a valve structure. A resilient annular seal member at the base of the tip forms a seal about the end of the discharge port. After withdrawing a fluid sample from the zwickel fitting, fluid can remain in the discharge port between the valve structure and the end of the discharge port.

U.S. Pat. No. 4,406,301 to Cerrato discloses a keg-tapping structure. The keg-tapping structure mounts a valve member or ball on a compressionally loaded conical spring. The keg-tapping structure of this patent does not provide a tap for use on a vat or brewery vessel.

U.S. Pat. No. 4,510,969 to Rodth discloses a connector for pressurized source of beverage concentrate. The connector has a first section and a second section. An extending arm of the second section engages an actuating member of the first section. The two sections are joined by their respective, complementary screw threads. The joining of the two sections separates the actuating member from an O-ring and opens the dispensing valve. The connector of this patent does not provide a tap for use on a vat or brewery vessel.

The industry lacks a sanitary sampling device and method for a sanitary sampling device. The industry lacks a means for tapping a closed, unidirectional flow channel. There is a need for such a device and a method for collecting a sample of a liquid from a vessel without contaminating the liquid in a fitting or the vessel.

BRIEF DESCRIPTION OF THE INVENTION

The invention includes a sanitary method for tapping a closed, unidirectional flow channel. The method includes the step of engaging a nipple with a coupling means. The nipple provides a channel through a wall of a vessel. The channel contains a fluid from the vessel. The method further includes an engaging step. The engaging step simultaneously (a) seals the nipple with the coupling means and (b) opens a stopping means of the nipple at an end of the channel engaging the coupling means to permit a unidirectional flow of the fluid from the vessel. Then the method involves collecting the fluid from the channel of the nipple in a collecting means. The step of disengaging the nipple and the coupling means then occurs. The disengaging step simultaneously (a) releases the nipple from the coupling means and (b) closes the stopping means of the nipple to terminate the unidirectional flow of the fluid. The invention includes a sanitary sampling device that performs this method.

DETAILED DESCRIPTION OF THE INVENTION

Figure 1:
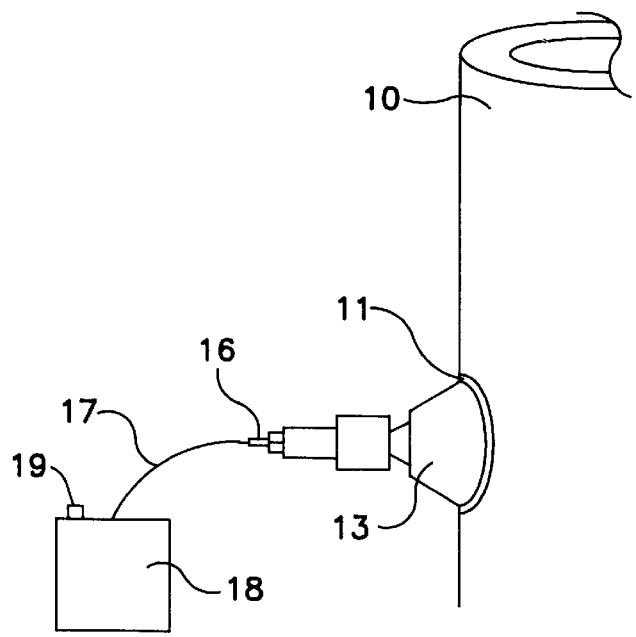
FIG. 1 illustrates the major components of the preferred sanitary sampling device of the invention.

The invention is a sanitary method for tapping a closed, unidirectional flow channel. The method includes the step of engaging a nipple or "a sampling port" with a coupling means or a "complementary sampling port." The nipple provides a channel through a wall of a vessel, such as a dairy, brewery, or pharmaceutical vessel. The channel contains a fluid, such as wort or malt beverage, from the vessel. The method further includes an engaging step. The engaging step simultaneously seals the nipple with the coupling means and opens a stopping means or valve of the nipple at an end of the channel engaging the coupling means to permit a unidirectional flow of the fluid. Then the method involves transferring the fluid through the channel of the nipple. The preferred embodiment of the invention at this step involves collecting the fluid from the channel of the nipple in a collecting means. The step of disengaging the nipple and the coupling means then occurs. The disengaging step simultaneously releases the nipple and coupling means and closes the stopping means of the nipple to terminate the unidirectional flow of the fluid. The invention includes a sanitary sampling device to perform this method.

The method includes the step of engaging a nipple or a sampling port with a coupling means or a complementary sampling port. The engaging step includes engaging a nipple with the coupling means. The nipple provides a first channel and the coupling means provides a second channel. The engaging step is performed by compressing, screwing, or otherwise joining the coupling means to the nipple. The engaging of the coupling means to the nipple simultaneously performs two steps of sealing the nipple and coupling means together, opening the channel or channels, and permitting a flow of liquid through the channel or channels.

The sealing procedure secures the nipple with the coupling means in a leak-proof relationship. The sealing procedure, for example, compresses a washer, an O-ring, a fluorohydrocarbon tape, or another conventional means between the complementary surfaces of the nipple and the coupling means. The sealing procedure prevents liquid flowing through the channel of the nipple from exposure to the atmosphere. In this manner, the liquid remains in a "closed system" as it flows into the channel of the coupling means and/or the collecting means.

The opening procedure breaks a seal between a stopping means of the nipple at an end of the channel of the nipple where the coupling means engages the nipple. The channel of the nipple is also aligned with any channel of the coupling means and/or collecting means. The opening procedure is performed by applying a force, such as a manual or automatic mechanical or electrical force, against the stopping means of the nipple. The force moves the stopping means into an opened position. The opening procedure can be performed by pressing the coupling means against the stopping means of the nipple. Such a procedure can include pressing a second stopping means of the coupling means against the first stopping means of the nipple. The compression of the opposing first and second stopping means can occur at the end of the first channel of the nipple and the end of the second channel of the coupling means such that the applied force moves both the first and the second stopping means into their respective open positions.

The opening procedure can be performed by numerous procedures. The opening procedure can include compressing opposing plates or stoppers of the nipple and coupling means. The opening procedure can include screwing the coupling means onto the nipple wherein the screwing process engages a mechanism that moves the first stopping means into an opened position. Another alternative procedure includes attaching a mechanism having teeth that engage a ball at the end of the channel of the nipple. The ball is pushed or pulled into the opened position depending upon its location within or outside of the channel of the nipple.

The opening procedure can include a locking procedure wherein a locking means maintains the engagement of the nipple with the coupling means. The locking procedure maintains the first stopping means and the second stopping means in their opened positions until the locking means is disengaged.

The engaging step permits a unidirectional flow of the fluid through the channel in the nipple. The unidirectional flow of the fluid can be through a single channel or multiple channels of the nipple. The unidirectional flow can follow several paths including a path between the stopping means and the wall of the channel, a path through the stopping means, or a path both through and around the stopping means.

The method includes the step of transferring the fluid through the channel of the nipple. This step in the preferred embodiment of the invention involves collecting the fluid from the channel of the nipple in a collecting means. The collecting step can be performed by collecting the fluid directly in a container or by collecting the fluid through a second channel of the coupling means and/or a conduit and then into the container. The collecting means can be controlled by adding a flow control device either before or after the coupling means. The preferred method maintains a closed system during the collecting step to prevent exposure of the fluid to the atmosphere.

An alternative method of this invention is a sanitary method for tapping a closed, unidirectional flow channel, but this alternative method inoculates the liquid in the vat or tank. The alternative method replaces the collecting step with an injecting step. The injecting step injects a gas, liquid, or particulate fluid from an external container through the nipple into the vat or tank. The fluid must be injected at a pressure in excess of the pressure in the vat or tank. All other steps, procedures, and devices remain the same. A procedure of controlling the pressure differential in the closed system and external to the port of the nipple can be used to determine the direction of the unidirectional flow of fluid through the nipple.

The disengaging step includes disengaging the nipple and the coupling means. The disengaging step releases the nipple and coupling means and breaks their seal. Simultaneously, this step closes the stopping means of the nipple and, optionally, a second stopping means of the coupling means and terminates the unidirectional flow of the fluid.

The releasing procedure breaks the seal between the nipple and the coupling means. The releasing procedure can be performed by a "quick release" mechanism wherein the seal created by an elastic washer or O-ring is broken and the decompression of the elastic washer or O-ring "springs" the coupling means away from the nipple. The releasing procedure can be performed by other methods including the coupling means from the nipple.

The closing procedure shuts the stopping means of the nipple and terminates the unidirectional flow of the fluid. The closing procedure removes the pressure that forces the stopping means of the nipple into an opened position. The release of this pressure moves the stopping means of the nipple into a closed position.

The closing procedure can be performed with a self-closing means or mechanism. A self-closing mechanism forces the stopping means of the nipple into a closed position when the coupling means is released from the nipple. A conventional mechanical or electrical device can close the stopping means and secure the stopping means in the closed position. Pressure differentials on opposite sides of the stopping means can also be used to close the stopping means.

The closing procedure can include an unlocking procedure wherein the locking means is disengaged to allow the nipple and the coupling means to separate. The unlocking procedure permits the stopping means and, optionally, the second stopping means, to close.

The disengaging step terminates the unidirectional flow of the liquid through the channel of the nipple. This step terminates the flow through the nipple without allowing air to enter the nipple, thereby preventing contamination of the fluid in the tank.

The invention includes a sanitary sampling device that performs the method of the invention. The device includes a means for tapping a closed, unidirectional flow channel, a coupling means, and a collecting means. The sanitary sampling device collects a sample from a tank without contaminating the fluid in the nipple or the tank.

The means for tapping a closed, unidirectional flow channel can be recessed in the wall of a vat or tank or can protrude from the wall of such a vessel. The means for tapping provides a channel through the wall of the vessel. When the means for tapping is recessed in the wall of the vat or tank, the structure and sealing means must ensure that residual liquid cannot collect in a location wherein contamination of a subsequent sample can occur.

The means for tapping can be operated by a variety of means to open and close a stopping means of the channel. The means for operating the stopping means can be mechanical or electrical. Mechanical means for operating the stopping means includes a spring and piston apparatus and/or a pressure differential apparatus. A pressure differential apparatus positions a valve according to the pressures of fluids on opposing sides of the valve. Electrical means for operating the stopping means can include a solenoid or similar device. The preferred embodiment of the apparatus use a nipple for the means for tapping a closed, unidirectional flow channel.

The means for tapping in the preferred embodiment of the invention is a nipple. The replacement of parts in the nipple of the preferred embodiment of the invention, such as a viton seal or spring, can be performed without replacing the entire nipple. This simplified repair procedure is significantly less than the cost of nipple replacement.

The nipple of the preferred embodiment of the invention has two ends. A first end of the nipple has a first connecting means for affixing the first end of the nipple to a vessel. A second end of the nipple extends outward from an outside wall of the vessel. The nipple can be a hollow protrusion extending into and/or outward from the wall of the vessel. The nipple provides a first channel for the means for tapping. The channel at the first end of the nipple is open to the inside of the vessel. The channel remains in contact with and full of the liquid that is contained in the vessel. The nipple has a stopping means at the second end of the nipple. The second end of the nipple is the end of the nipple that engages the coupling means.

The affixing means for connecting the first end of the nipple to a vessel can include various structures. The first end of the nipple can be welded directly to the vessel or can be affixed to an adapter that is welded to the vessel. The nipple can also include internal or external threads as affixing means. Other affixing means can also be used.

The stopping means can include various structures. The stopping means can be any structure that provides a self-sealing means to the channel of the means for tapping. The stopping means can include a plate, a plate with a nipple extending outward from the center, a hollow or solid ball, an inflatable member, or other structure or combination of structures. The stopping means can be a stopper located either on the inside or the outside of the channel at the second end of the nipple. The stopper means can be self-sealing by placing an O-ring, a seal, or a washer at the end of the channel of the nipple.

The nipple can include a locking means to maintain the engaged condition of the nipple and the coupling means. The locking means in the preferred embodiment of the invention retains the first stopping means or, optionally, the first stopping means and the second stopping means in an opened condition or position until the locking means is disengaged.

The coupling means of the preferred embodiment of the invention has two ends. A first end of the coupling means engages the means for tapping or nipple. The coupling means can be adapted with a second stopping means. A second end of the coupling means has a connecting means for affixing the coupling means to a vessel or a collecting means. The coupling means has a channel for transferring fluid. The coupling means of the preferred embodiment of the invention transfers fluid from a first channel of the nipple through a second channel of the coupling means into the collecting means.

The coupling means can include a locking means to maintain the engaged condition of the nipple and the coupling means. The locking means can be the same as the locking means described for the means for tapping or nipple. The preferred embodiment of the invention has complementary portions of a locking means to engage and hold the coupling means to the nipple.

The stopping means can be the same structure as described for the stopping means of the means for tapping or nipple. The stopping means can be located either on the inside or on the outside of the channel at the first end of the coupling means. A self-sealing means can also be provided. The preferred embodiment of the invention has a first stopping means in the nipple that abuts with a second stopping means in the coupling means. The two stopping means open when the coupling means engages the nipple.

Both the nipple and the coupling means of the invention can have threaded sections to provide a sanitary seal. A seal between such threaded sections is internal to the threads. The seal can be provided, for example, by a gasket between the face of the well and nipple or between the coupling means and attachment. A sanitary threaded section prevents liquid from becoming entrapped in the threads. A sanitary seal is a structure having a gasket, washer, or other sealing means immediately adjacent and between two abutting channels of a nipple and a coupling means.

The connecting means for affixing the second end of the coupling means to a collecting means can have a variety of structures. The connecting means can include a weld or internal or external threads. The connecting means can also be a nipple or a hex nipple. The connecting means can affix a conduit or a conduit with a flow control means. The conduit can be affixed to the collecting means. The connecting means can be a variety of accessory connectors.

Anaerobic closed systems can have accessory connectors including a Luer fitting for a sterile syringe or a B–D vacutainer system using a septum style attachment to the coupling means. Aerobic open systems can have accessory connectors including a tubing and clamp system or autoclavable valve wherein the liquid is dispensed into a sterile container. Accessory connectors can permit the injection of material into a vessel. A desirable accessory connector is used with vinyl tubing, such as Tygon™ brand tubing, to indicate the liquid level in the vessel. Such a "sight glass" is sanitary and can be cleaned with a clean-in-place system when the clean-in-place solution supply is connected to the upper fittings, including tubing, and the lower fittings of a brewery vessel.

An accessory can be connected to the connecting means to inject an inert gas or similar substance through the nipple. Such an injector is useful in clearing sediment from the nipple. For example, a carbon dioxide pistol can be adapted to inject a burst of carbon dioxide gas through a nipple to clear its channel.

A vessel can be affixed to the coupling means. The vessel can be affixed directly to the second end of the coupling means or indirectly by a conduit or hose. The vessel can be empty or can contain a fluid of gas, liquid, or particulate matter. The interior of the vessel can be in a vacuum, at atmospheric pressure, or under a pressure above atmospheric pressure. The preferred embodiment of the invention has a collecting means for a vessel.

The collecting means of the preferred embodiment of the invention collects a sample from the channel of the nipple. The collecting means can include a vacuum bag, a vented vessel, an open vessel, a syringe, and a sample-collecting conduit with a flow control means. The flow control means can be a valve, a pressure or pinch clip, a self-sealing stopper, a pet-cock, or a self-sealing pin. The preferred embodiment of the collecting means includes a sample-collecting conduit, having a pinch clip, wherein the conduit is affixed to a closed, vented bag.

The invention provides a sanitary device for use as a tapping means on a brewery vessel. The sanitary device collects a sample of a liquid from the brewery vessel without contaminating the liquid in the brewery vessel or leaving liquid exposed to air in a spout of the tap. The invention closes the tapping means at the end or terminus of the port or channel. The channel closes immediately to prevent liquid from draining from a spigot. No liquid remains in the sanitary device that is exposed to air and/or microbes.

The nipple and coupling means of this invention can be cleaned with a "tank-in-place cleaning system." Such a cleaning system permits a brewery vessel such as a vat or tank to be cleaned along with its auxiliary components without disassembly of the components.

FIG. 1 illustrates the major components of this invention. A tank 10 is fitted with a tank adaptor 11. The tank adaptor 11 has a connecting means to securely receive a nipple 13 with a first seal (not shown) interposed between the adaptor 11 and the nipple 13. The nipple 13 receives and securely seals with a coupler 14. The coupler 14 has a connecting means to receive a hex nipple 16 securely with a second seal (not shown) interposed between the coupler 14 and hex nipple 16. The hex nipple 16 is affixed to a hose 17. A pinch clip (not shown) can be applied to the hose 17 to prevent the flow of liquid through the hose 17. The hose 17 is affixed to a close vacuum bag 18. The closed vacuum bag 18 has a one-way valve or vent 19 for releasing excess fluid collected from the tank 10.

Figure 2:
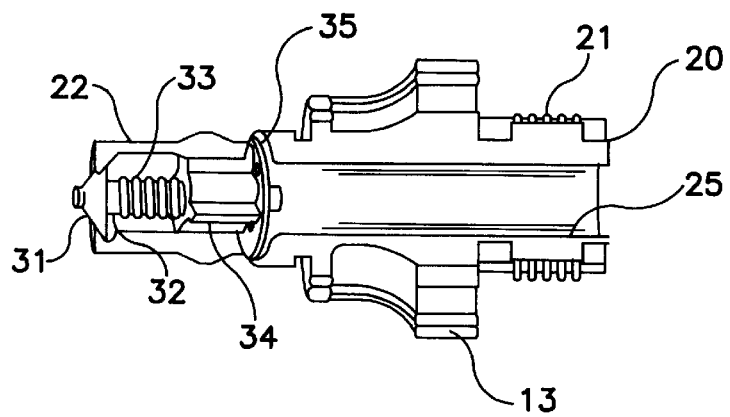
FIG. 2 illustrates a cut-away view of a nipple.

FIG. 2 illustrates a cross-section of a nipple 13. The nipple 13 has two ends. A first end 20 of the nipple 13 has threads 21 for affixing the first end 20 of the nipple 13 to the tank 10. A second end 22 of the nipple 13 extends outward from the tank 10. The nipple 13 has a first channel 25 and a first stopping means. The illustration of the outward extending second end of the nipple 13 is "cut away" to expose the stopping means of the nipple 13.

The first stopping means includes a plate 31. The plate 31 is mounted to a rod 32. A spring 33 is over the rod 32 and applies tension against the plate 31 away from a block 34. The block 34 is mounted against a washer 35. The second end 22 of the nipple 13 has a locking ring 36 for a complementary locking means of a coupler.

Figure 3:
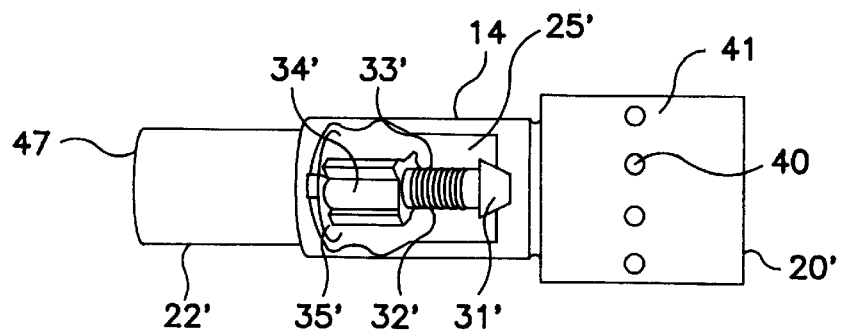
FIG. 3 illustrates a cut-away view of a coupler.

FIG. 3 illustrates coupler 14. The coupler 14 has a "quick-release" connecting apparatus that includes a series of ball bearings 40 and a spring-loaded slide 41. The spring-loaded slide 41, when pulled towards the center of the coupler 14, loosens the ball bearings 40 in their sockets. The ball bearings 40 roll over the locking ring 36 of the nipple 13. When the spring-loaded slide 41 is released, the ball bearings 40 lock in their sockets and do not roll over the locking ring 36. The coupler 14 is fitted with a second stopping means that is similar to the first stopping means of the nipple 13. The coupler 14 has a connector 47 for receiving a hose 17. The coupler 14 provides a "female" structure that is complementary to the "male" structure of the nipple 13.

FIG. 3 includes a cross-section of the coupler 14. The coupler 14 has two ends. A first end 20' of the coupler 14 has a second stopping means and a means for locking the coupler 14 to the nipple 13. A second end 22' of the coupler 14 has a connector 47. The connector 47 receives and holds the hose 17. A hex nipple 16 can be affixed to the connector 47 to receive the hose 17. The coupler 14 has a channel 25'. The first end 20' of the coupler 14 has a stopping means. The stopping means includes a plate 31'. The plate 31' is mounted to a rod 32'. A spring 33' is over the rod 32' and applies tension against the plate 31' away from a block 34'. The block 34' is mounted to a washer 35'.

Figure 4:
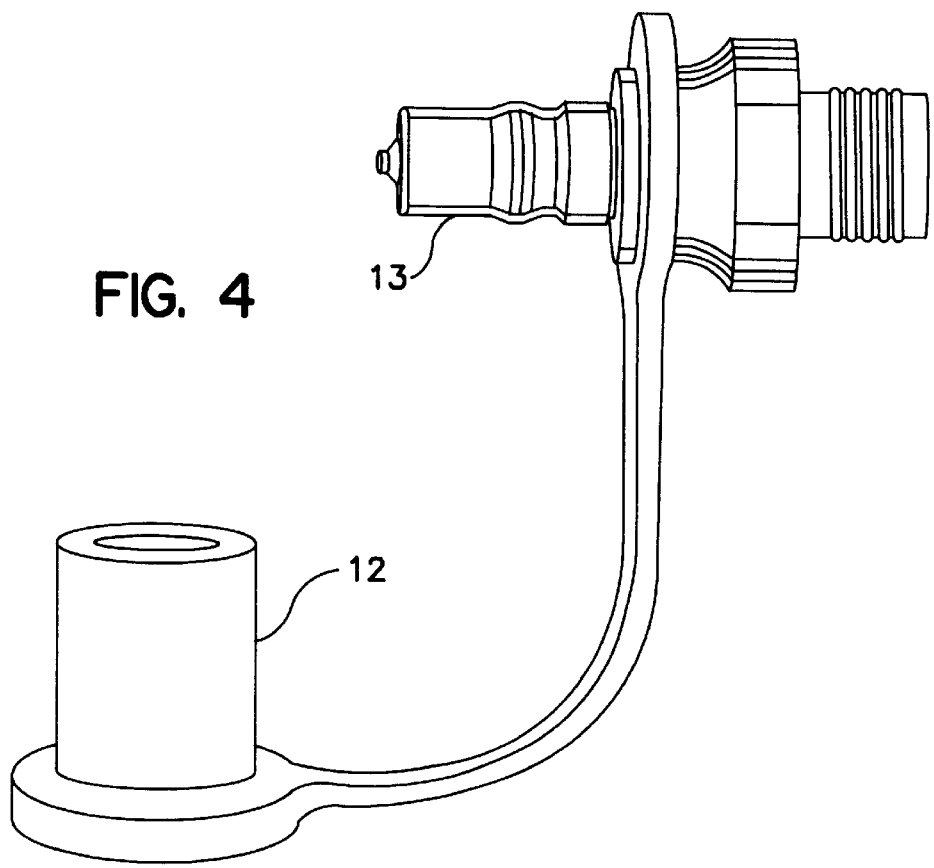
FIG. 4 illustrates an open cover for the nipple.

FIG. 4 illustrates an open cover 12. The cover 12 is suspended from the exposed nipple 13.

Figure 5:
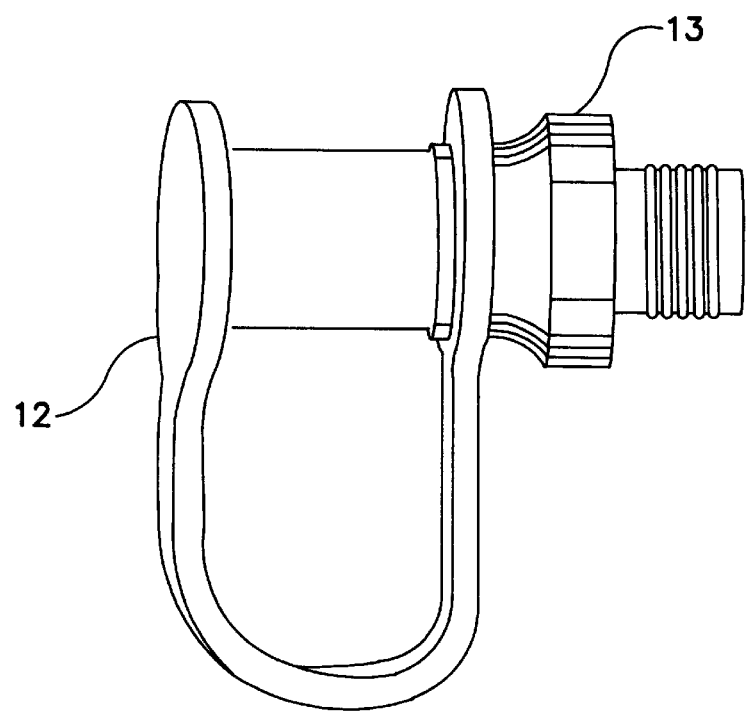
FIG. 5 illustrates a closed cover for the nipple.

FIG. 5 illustrates a closed cover 12. The cover 12 is plastic and snaps onto the nipple 13 to prevent contamination.

The operation of the preferred embodiment of the invention mounts a female coupler 14 over the nipple 13. The plate 31' of the coupler 14 opposes and engages the plate 31 of the nipple 13. The engagement of the opposing plates pushes each plate inward into its respective fitting. The movement of the plate 31 inward compresses the spring 33 and pushes the rod 32 through the block 34. This movement opens an orifice in the channel 25. This condition permits liquid to flow from the channel 25 of the nipple 13 through the orifice and through the external outlet of the second end 22 of the nipple 13. When the coupler 14 is engaged with the nipple 13, the movement of the plate 31' inward compresses the spring 33' and pushes the rod 32' through the block 34'. This movement opens an orifice in the channel 25' of the coupler 14. During the engagement of the coupler 14 with the nipple 13, the liquid flows from the channel 25' of the coupler 14 through the orifice and exits the coupler 14.

Figure 6:
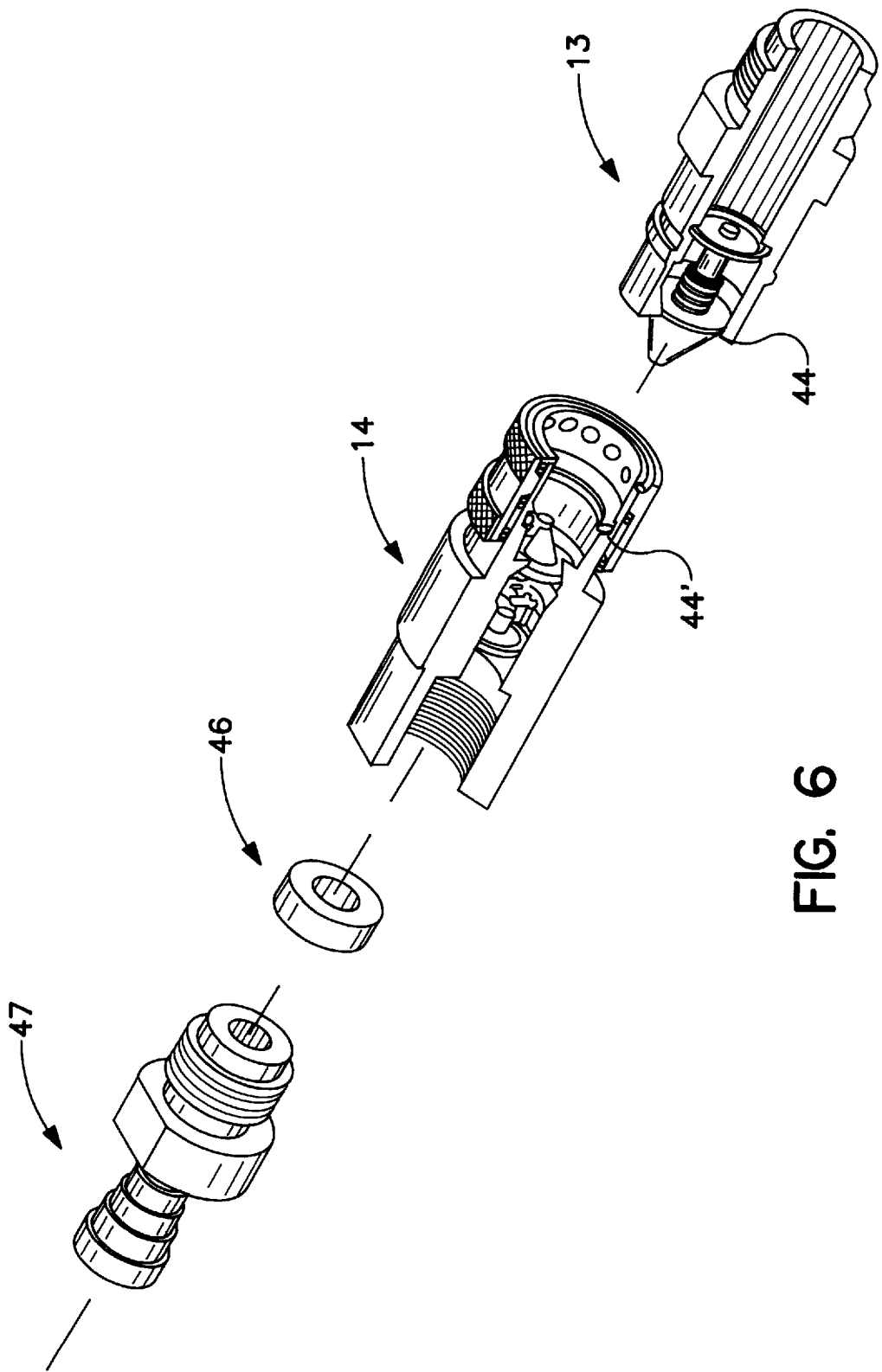
FIG. 6 illustrates the component assembly of the preferred embodiment of the invention.

FIG. 6 illustrates the assembly of the nipple and the coupling means of the preferred embodiment. The nipple 13 inserts into the coupler 14. A sanitary seal is provided between the nipple 13 and the coupler 14 by a fluorohydrocarbon polymer ring 44 in the nipple 13 and a viton seal 44' in the coupler 14. A BUNA-N nitrile rubber gasket 46 provides a sanitary seal between the coupler 14 and an accessory connector 47.

Figure 7:
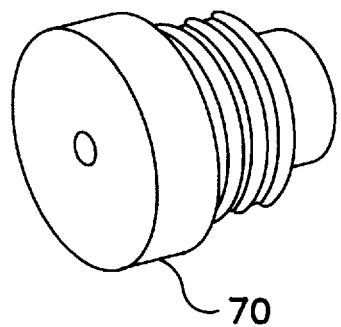
FIG. 7 illustrates an infusion adaptor.

FIG. 7 illustrates an alternative accessory connector. The accessory connector of this embodiment is an infusion adaptor 70.

Figure 8:
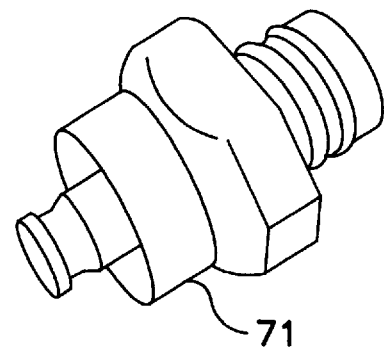
FIG. 8 illustrates a syringe adaptor.

FIG. 8 illustrates an alternative accessory connector. The accessory connector of this embodiment is a syringe adaptor 71.

Figure 9:
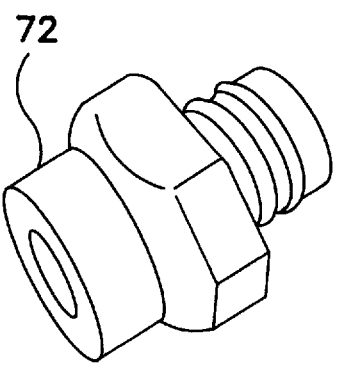
FIG. 9 illustrates a glass tube adaptor.

FIG. 9 illustrates an alternative accessory connector. The accessory connector of this embodiment is a glass tube adaptor 72.

Figure 10:
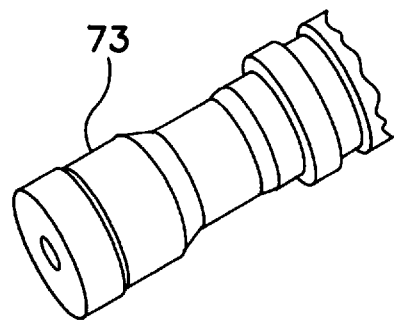
FIG. 10 illustrates an infusion coupler.

FIG. 10 illustrates an alternative accessory connector. The accessory connector of this embodiment is an infusion coupler 73.

Figure 11:
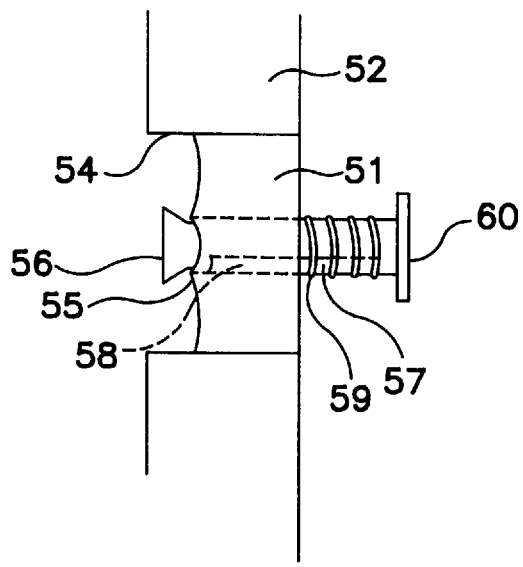
FIG. 11 illustrates an alternative embodiment of a nipple.

FIG. 11 illustrates an alternative embodiment of a nipple 51. The nipple 51 is embedded and welded into a tank wall 52. Threads 54 are in the orifice of the tank wall 52 for the nipple 51. The stopper 56 abuts a sanitary seal 55 and is mounted to a rod 57. The rod 57 has a longitudinal channel 58 partially cut into its length. A compressed spring 59 exerts tension between the body of the nipple and an end cap 60 of the rod 57.

Figure 12:
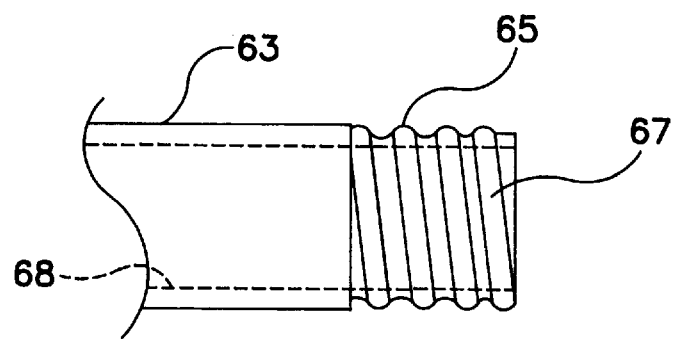
FIG. 12 illustrates an alternative embodiment of a coupler.

FIG. 12 illustrates an alternative embodiment of a coupler 63. The coupler 63 is the "male" complement to the "female" threads 54 in the tank wall 52 of FIG. 6. The coupler 63 has external threads 65 and a partial internal thread 67. The partial internal thread 67 is in a channel 68. The partial internal thread 67 engages the stopper 56 of the nipple 51 and pulls the stopper 56 open as the coupler 63 is turned.

The engagement of the coupler 63 with the nipple 51 pulls the stopper 56 and rod 57 into the coupler. The channel 58 in the rod 57 provides an opening in the nipple 51. Fluid flows from the tank through the channel 58 and into the coupler 63. The disengaging of the coupler 63 from the nipple 51 closes the stopper 56 and terminates the unidirectional flow of liquid.

The sanitary sampling device of the invention provides the desirable result of terminating the flow of liquid from the tank at the end of the channel of the nipple. No nozzle or spout extends beyond the orifice of the nipple. Therefore, no residual liquid collects once the plate closes against the end of the channel of the nipple. The liquid inside the nipple remains in contact with the liquid in the tank and has no greater or lesser concentration of contaminants, microbes, or intermediate compounds than the liquid in the tank. The liquid within the nipple remains isolated from oxygen and, thereby, prevents the growth of aerobic microbes.

The invention is desirable for a brewery vessel with a clean-in-place connection system. The clean-in-place connection system permits the brewery vessel and its attachments to be cleaned without significant disassembly. An additional benefit is provided by the invention, when used with such cleaning systems, in that the risk of chemical spills or accidental release of clean-in-place tubing is minimized. The preferred embodiment of the invention is leak-proof to about 1,500 pounds per square inch of pressure.

Also, the invented tapping means is tamper-resistant and relatively inexpensive to install, operate, and/or repair. The tapping means is also compatible with most existing portable analyzing equipment.

What is claimed is:

1. In a method for sampling the contents of a vessel used for preparing, treating, or holding liquid substances so that the contents can be analyzed for bacterial contamination, the improvement that comprises tapping a closed, unidirectional flow channel by engaging a nipple with a coupling means, wherein said nipple provides a channel for fluid flow, and wherein said engaging step simultaneously:
  (a) seals said nipple with said coupling means and
  (b) opens a stopping means of said nipple at an end of said channel engaging said coupling means
  (c) thereby permitting a unidirectional flow of said fluid;

transferring said fluid through said channel of said nipple into said coupling means and, thereafter, into a sterile sample receiving means;

disengaging said nipple and said coupling means after said sampling has been completed; wherein said disengaging step simultaneously:
  (a) releases said nipple from said coupling means and
  (b) closes said stopping means of said nipple to terminate said unidirectional flow of said fluid; and then cleaning said disengaged coupling means and any other means attached thereto to remove residual sample prior to further sampling; whereby a false positive in a subsequent sample produced by contamination from the residual sample is avoided.

2. The method of claim 1 wherein the step of engaging said nipple with said coupling means includes abutting a first stopping means in said nipple and a second stopping means in said coupling means.

3. In a method for sampling the contents of a brewery tank used for preparing, treating, or holding brewery fluid so that the contents can be analyzed for bacterial contamination, the improvement that comprises tapping a closed, unidirectional flow channel by compressing a nipple mounted on said brewery tank and having a first spring-loaded stopper with a coupler having a second spring-loaded stopper that abuts said first spring-loaded stopper, wherein said compressing step simultaneously:
  (a) seals said nipple with said coupler and
  (b) opens said first stopper and said second stopper, thereby permitting a unidirectional flow of a brewery fluid from said brewery tank;

collecting said brewery fluid from said nipple and said coupler in a sterile container; and disengaging said nipple and said coupler after said sampling has been completed; wherein said disengaging step simultaneously:

(a) closes said first stopper and said second stopper and (b) terminates said unidirectional flow of said brewery fluid without exposure of said brewery fluid to the atmosphere; and then cleaning said disengaged coupling means and any other means attached thereto to remove residual sample prior to further sampling; whereby a false positive in a subsequent sample produced by contamination from the residual sample is avoided.

\* \* \* \* \*